(12) United States Patent
Nessler et al.

(10) Patent No.: US 9,000,267 B2
(45) Date of Patent: Apr. 7, 2015

(54) STRESS TOLERANT TRANSGENIC PLANTS OVER-EXPRESSING ASCORBIC ACID AND CELL WALL SYNTHESIS GENES

(75) Inventors: Craig L. Nessler, College Station, TX (US); Argelia Lorence, Jonesboro, AR (US); Boris Chevone, St. Charles, MO (US); Pedro Mendes, Farmington, CT (US)

(73) Assignee: Virginia Tech Intellectual Properties, Inc., Blacksburg, VA (US)

( * ) Notice: Subject to any disclaimer, the term of this patent is extended or adjusted under 35 U.S.C. 154(b) by 1119 days.

(21) Appl. No.: 11/908,551

(22) PCT Filed: Jun. 23, 2005

(86) PCT No.: PCT/US2005/022179
§ 371 (c)(1),
(2), (4) Date: May 27, 2008

(87) PCT Pub. No.: WO2006/104503
PCT Pub. Date: Oct. 5, 2006

(65) Prior Publication Data
US 2008/0250526 A1   Oct. 9, 2008

Related U.S. Application Data

(60) Provisional application No. 60/665,370, filed on Mar. 28, 2005.

(51) Int. Cl.
| | |
|---|---|
| *A01H 1/00* | (2006.01) |
| *A01H 5/00* | (2006.01) |
| *C07H 21/04* | (2006.01) |
| *C12N 5/14* | (2006.01) |
| *C12N 15/09* | (2006.01) |
| *C12N 9/02* | (2006.01) |
| *C12N 9/04* | (2006.01) |
| *C12N 15/82* | (2006.01) |

(52) U.S. Cl.
CPC ............ *C12N 9/0069* (2013.01); *C12N 9/0006* (2013.01); *C12N 15/8243* (2013.01); *C12N 15/8261* (2013.01); *C12N 15/8273* (2013.01)

(58) Field of Classification Search
None
See application file for complete search history.

(56) References Cited

U.S. PATENT DOCUMENTS

2004/0185562 A1* 9/2004 Schroeder et al. ............ 435/455

FOREIGN PATENT DOCUMENTS

EP         1033405 A2 * 6/2000

OTHER PUBLICATIONS

Lorence et al. (Plant Physiology, 134:1200-1205, 2004).*
Lorence et al. (Plant Physiology, 134:1200-1205, Mar. 1, 2004).*
Jain et al. "Metabolic Engineering of an Alternative Pathway for Ascorbic Acid Biosynthesis in Plants", Mocelular Breeding 6, 2000, pp. 73-78 Veljovic-Jovanovic et all., "Low Ascorbic Acid in the vtc-1 Mutant of Arabidopsis is associated with Decreased Growth and Interacellular Redistribution of the Antioxidant System", Plant Physiology, Oct. 2001, Vol.
Lorence et al. "myo-Inositol Oxygenase Offers a Possible Entry Point into Plant Ascorbate Biosynthesis", Plant Physiology, Mar. 2004, vol. 134, pp. 1200-1205.

* cited by examiner

*Primary Examiner* — Vinod Kumar
(74) *Attorney, Agent, or Firm* — Whitham, Curtis, Christofferson & Cook, P.C.

(57) ABSTRACT

Methods are provided for increasing plant growth rate, biomass and tolerance to stress by genetically engineering plants to contain and express a gene of the ascorbic acid synthesis-cell wall synthesis network (e.g. GlcUA reductase, GLOase or MIOX). Transgenic plants that are genetically engineered in such a manner are also provided.

17 Claims, 9 Drawing Sheets

ATGGCAAATCCGAGCACATTTTCAAGCTCAACACCAGCGCTAAGTTCCCTTCGGT
GGGTCTTGGAACATGGCAAGCTTCCTGGCCTCGTCGGTGATGCAGTCGCCGCG
GCCGTTAAGATTGGCTATCGTCACATTGATTGTGCTCAGATCTATGGCAACGAAAAA
GAGATTGGGGCAGTTCTGAAAAAATTGTTTGAAGACAGAGTAGTGAAACGCGAGGA
TTTGTTCATCACCTCCAAACTCTCAAGGATCTGCAGCTTGAATACGTCGATCTTTATCTGAT
GGCATTGAACAGAACTCTCAAGGATCTGCAGCTTGAATACGTCGATCTTTATCTGAT
ACACTGGCCTGCACGGATAAAGAAAGGTTCTGTTGGAATAAAGCCAGAGAACCTTT
TGCCTGTAGATATTCCTAGTACATGGAAAGCGATGGAAGCACTATACGATTCGGGC
AAGGCACGAGCCATAGGTGTAAGCAATTTCTACCAAGAAACTAGCTGATCTCTT
GGAGTTAGCTCGTGTTCCTCCTGCTGTTAATCAGGTCGAATGTCATCCTTCTTGGC
GACAAACTAAGCTACAAGAATTCTGCAAATCCAAAGGGGTTCACCTAAGTGCATACT
CGCCATTAGGTTCTCCAGGACAACATGGCTGAAGAGCGATGTTTTGAAGAACCCG
ATACTGAATATGGTTGCGGAAAAACTCGGAAAGAGTCCTGCGCAAGTCGCCCTTCG
TTGGGGACTCCAAATGGGTCACAGTGGTCACTTCCCAAGAGTACAAATGAGGATCCAA
TCACGAATTCTGGATCCGATACGTAA

*Figure 7A*

MANPSTFFKLNTSAKFPSVGLGTWQASPGLVGDAVAAAVKIGYRHIDCAQIYGNEKEIG
AVLKKLFEDRVVKREDLFITSKLWCTDHDPQDVPEALNRTLKDLQLEYVDLYLIHWPARI
KKGSVGIKPENLLPVDIPSTWKAMEALYDSGKARAIGVSNFSTKKLADLLELARVPPAVN
QVECHPSWRQTKLQEFCKSKGVHLSAYSPLGSPGTTWLKSDVLKNPILNMVAEKLGKS
PAQVALRWGLQMGHSVLPKSTNEDPITNSGSDT*

*Figure 7B*

```
Query    1    MANPSTFFKLNTSAKFPSVGLGTWQASPGLVGDAVAAAVKIGYRHIDCAQIYGNEKEIGA  60
Sbjct    1    MAN TFFKLNT AKFPSVGLGTWQASPGLVGDAVAAAVKIGYRHIDCAQIYGNEKEIGA
              MANAITFFKLNTGAKFPSVGLGTWQASPGLVGDAVAAAVKIGYRHIDCAQIYGNEKEIGA  60

Query   61    VLKKLFEDRVVKREDLFITSKLWCTDHDPQDVPEALNRTLKDLQLEYVDLYLIHWPARIK  120
Sbjct   61    VLKKLFEDRVVKREDLFITSKLWCTDHDPQDVPEALNRTLKDLQLEYVDLYLIHWPARIK
              VLKKLFEDRVVKREDLFITSKLWCTDHDPQDVPEALNRTLKDLQLEYVDLYLIHWPARIK  120

Query  121    KGSVGIKPENLLPVDIPSTWKAMEALYDSGKARAIGVSNFSTKKLADLLELARVPPAVNQ  180
Sbjct  121    KGSVGIKPENLLPVDIPSTWKAMEALYDSGKARAIGVSNFSTKKLADLLELARVPPAVNQ
              KGSVGIKPENLLPVDIPSTWKAMEALYDSGKARAIGVSNFSTKKLADLLELARVPPAVNQ  180

Query  181    VECHPSWRQTKLQEFCKSKGVHLSAYSPLGSPGTTWLKSDVLKNPILNMVAEKLGKSPAQ  240
Sbjct  181    VECHPSWRQTKLQEFCKSKGVHLSAYSPLGSPGTTWLKSDVLKNPILNMVAEKLGKSPAQ
              VECHPSWRQTKLQEFCKSKGVHLSAYSPLGSPGTTWLKSDVLKNPILNMVAEKLGKSPAQ  240

Query  241    VALRWGLQMGHSVLPKSTNEDPI    263
Sbjct  241    VALRWGLQMGHSVLPKSTNE   I
              VALRWGLQMGHSVLPKSTNEGRI    263
```

Figure 8

STRESS TOLERANT TRANSGENIC PLANTS OVER-EXPRESSING ASCORBIC ACID AND CELL WALL SYNTHESIS GENES

CROSS-REFERENCE TO RELATED APPLICATIONS

This application is a 371 of International Application Number PCT/US2005/022179 filed Jun. 23, 2005, which claims benefit of U.S. Provisional Patent Application Ser. No. 60/665,370 filed Mar. 28, 2005, and which are incorporated herein by reference.

BACKGROUND OF THE INVENTION

1. Field of the Invention

The invention generally relates to methods for increasing plant growth, biomass, and stress tolerance. In particular, the invention provides methods for increasing plant growth, biomass and stress tolerance by genetically engineering plants to contain and express a gene of the ascorbic acid synthesis-cell wall synthesis network.

2. Background of the Invention

Adequate food supplies, the availability of renewable energy sources, and global warming are among the most pressing issues facing the world today. With respect to the world's food supply, explosive population growth, particularly in developing nations, threatens to, or in some cases has already, outstripped the capacity of poorer nations to feed their citizens.

Regarding renewable energy sources, there is an ever increasing interest in biological sources, such as ethanol and oils produced from plants, as alternatives to fossil fuels. The interest is spurred not only by the finite nature of fossil fuel reserves, but also by the problems created by emissions that result from their use. Since 1800, atmospheric concentrations of $CO_2$ have increased by more than 25%, primarily from the combustion of fossil fuels. Carbon dioxide in the atmosphere absorbs infrared energy and prevents such energy from leaving the atmosphere, and is thus often referred to as a "greenhouse" gas. Increasing levels of greenhouse gases in the atmosphere may contribute to an increase in average global temperatures, resulting in adverse climate changes otherwise known as global warming.

A potential solution to these problems could be an overall increase in plant growth and biomass, particularly for plants that are used for food and/or fuel production. An increase in aboveground biomass could represent an important addition to renewable energy and food production, while a concomitant enhancement of belowground biomass could significantly contribute to carbon sequestration to lower tropospheric greenhouse gases.

The prior art has thus far failed to provide a reliable means to safely and effectively transform plants to exhibit an increased growth rate, as well as increased aboveground and belowground biomass production.

SUMMARY OF THE INVENTION

It is an object of this invention to provide a method of increasing the growth rate, biomass (both above- and belowground), and stress (e.g. salt) tolerance of plants. The method is based on the surprising discovery that genetically engineering a plant to contain and express at least one gene from the ascorbic acid (AsA) and cell wall polysaccharide synthesis network causes the plant to exhibit an increase in growth rate, biomass, and tolerance to stress. Increases in growth rate are advantageous in that this opens the possibility for harvesting mature crops even in areas with short growing seasons. Alternatively, in areas with longer growing seasons, multiple crops may be planted and harvested consecutively from the same plot. Increases in aboveground biomass result in greater quantities of produce per plant, while at the same time, concomitant increases in belowground biomass result in sequestration of larger quantities of carbon, helping to alleviate the problem of greenhouse gas buildup. Similarly, increases in stress tolerance of plants opens opportunities to successfully cultivate crops or other plants of interest under conditions that were not previously possible, e.g. in areas with high soil salinity.

The present invention provides a method for increasing the growth rate, biomass or stress tolerance of a plant. The method comprises the step of genetically engineering the plant to contain and overexpress at least one functional gene product of an ascorbic acid synthesis-cell wall synthesis network. Examples of the functional gene products include myo-inositol oxygenase, glucuronic acid reductase, L-gulono-1,4-oxidase, glucuronate kinase, L-gulonate lactonase, gulono-1,4-lactone dehydrogenase, GDP-mannose pyrophosphorylase, GDP-mannose-3,5-epimerase, GDP-L-galactose phosphodiesterase, L-galactose 1-phosphate phosphatase, L-galactose-1-dehydrogenase, L-galactono-1,4-lactone dehydrogenase, methylgalacturonate methyl-esterase, D-galacturonate reductase, L-galactonate lactonase, and dehydroascorbate reductase. According to the method, either wet biomass or dry biomass, or both, of the plant is increased. In addition, the salt tolerance of the plant is increased. Exemplary plants include *Arabidopsis*, lettuce, tobacco, soybeans, potato, tomato, canola, rice, corn, wheat and hybrid poplar. In some cases, the step of genetically engineering the plant causes an increase in the level of vitamin C of the plant. In other cases, the step of genetically engineering the plant does not cause an increase in the level of vitamin C of the plant.

The invention also provides a transgenic plant that is genetically engineered to contain and over-express at least one functional gene product of an ascorbic acid synthesis-cell wall synthesis network. Examples of functional gene products include myo-inositol oxygenase, glucuronic acid reductase, L-gulono-1,4-oxidase, glucuronate kinase, L-gulonate lactonase, gulono-1,4-lactone dehydrogenase, GDP-mannose pyrophosphorylase, GDP-mannose-3,5-epimerase, GDP-L-galactose phosphodiesterase, L-galactose 1-phosphate phosphatase, L-galactose-1-dehydrogenase, L-galactono-1,4-lactone dehydrogenase, methylgalacturonate methyl-esterase, D-galacturonate reductase, L-galactonate lactonase, and dehydroascorbate reductase. In some embodiments, the transgenic plant exhibits increased biomass. In some embodiments, either wet biomass or dry biomass, or both, is increased. In some embodiments, the plant exhibits increased stress tolerance and or increased salt tolerance. The transgenic plant may be, for example, *Arabidopsis*, lettuce, tobacco, soybeans, potato, tomato, canola, rice, corn, wheat and hybrid poplar. In some embodiments, the transgenic plant exhibits an increase in a level of vitamin C. In other embodiments, the transgenic plant does not exhibit an increase in a level of vitamin C.

The invention also provides an isolated and substantially purified plant glucuronic acid (GlcUA) reductase enzyme. The plant glucuronic acid reductase enzyme may be translated from a cloned plant glucoronic acid reductase gene. In one embodiment, the amino acid sequence of the plant GlcUA reductase enzyme is represented by SEQ ID NO: 8. In one embodiment, the cloned plant GlcUA reductase gene has a nucleotide sequence represented by SEQ ID NO: 7.

The invention also provides an isolated and substantially purified nucleotide sequence encoding a plant GlcUA reductase enzyme. In one embodiment, the isolated and substantially purified nucleotide sequence is represented by SEQ ID NO: 7. The invention further provides a vector comprising the nucleotide sequence represented by SEQ ID NO: 7.

In one embodiment of the transgenic plant of the invention, the at least one functional gene product of an AsA synthesis-cell wall synthesis network is a plant GlcUA reductase enzyme. In some cases, the plant GlcUA reductase enzyme is translated from a cloned plant GlcUA reductase gene, which may have a nucleotide sequence represented by SEQ ID NO: 7. Further, the amino acid sequence of the plant GlcUA reductase enzyme may be represented by SEQ ID NO: 8.

The invention also provides a method of increasing sequestration of carbon from the atmosphere by a plant. The method comprises the step of genetically engineering the plant to contain and over-express at least one functional gene product of an ascorbic acid synthesis-cell wall synthesis network, such that over-expression of the at least one functional gene product results in an increase in underground biomass of the plant and a consequent increase in carbon sequestered by the plant.

BRIEF DESCRIPTION OF THE DRAWINGS

FIGS. 7A and B show: A, the nucleotide sequence (SEQ ID NO: 7), and B, the amino acid sequence (SEQ ID NO: 8) of plant GlcUA reductase amplified from Arabidopsis leaf.

FIG. 8. Protein alignment of the plant GlcUA reductase from Arabidopsis as amplified versus the At2g37770 sequence (GeneBank Accession No. ACC23647). Top line, SEQ ID NO: 8; middle line, SEQ ID NO: 10; bottom line, SEQ ID NO: 9, FIG. 9. Vitamin C level of vtc-1-1 mutant, transformed with plant GlcUA reductase from Arabidopsis (T2 generation). Y axis is vitamin C level in µmol/gram of fresh weight; X axis represents plants, each one representing a different transformation event. (Arabidopsis plants were transformed with Agrobacterium tumefaciens; the T-DNA inserts into the plant genome randomly.)

DETAILED DESCRIPTION OF THE PREFERRED EMBODIMENTS OF THE INVENTION

Figure 1:
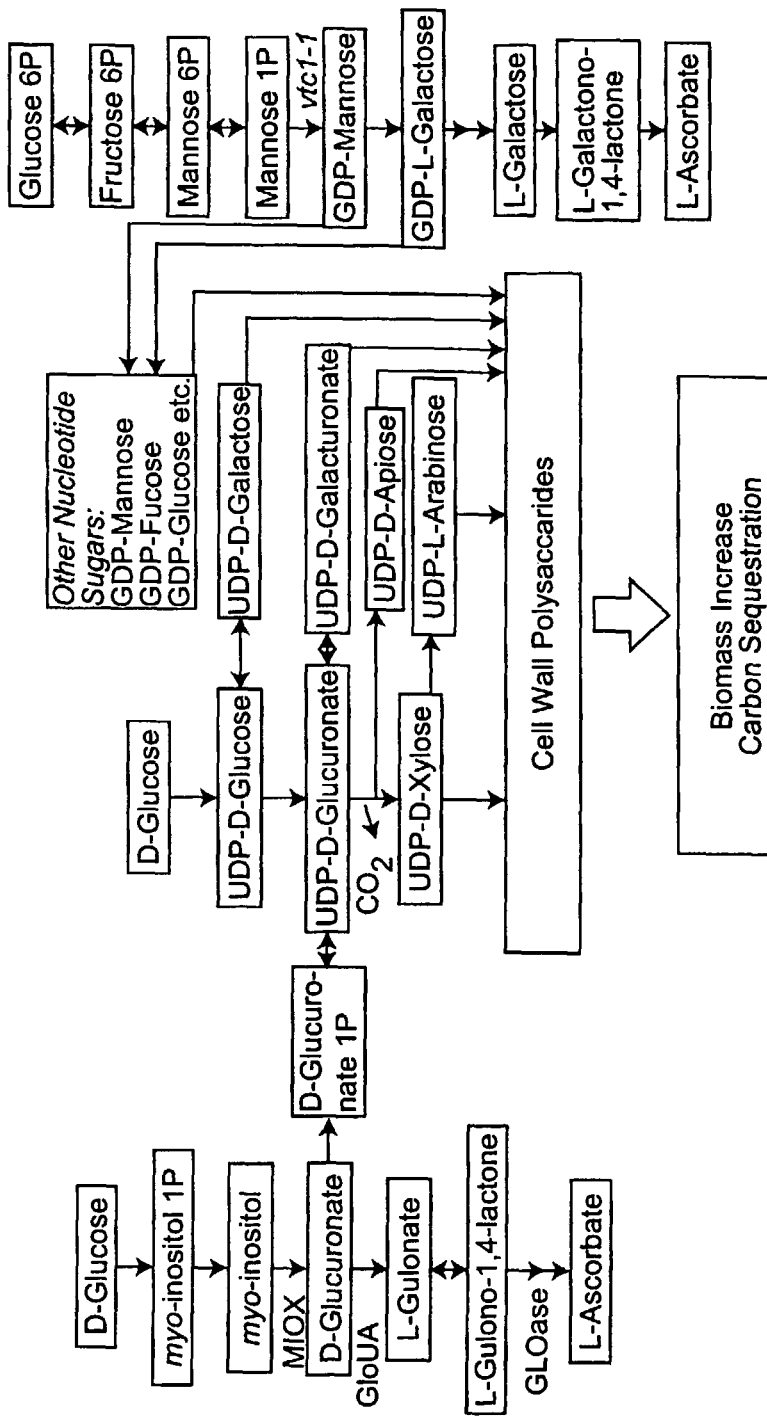
FIG. 1. Ascorbate (*) and cell wall polysaccharide biogenesis (☆) network. The mannose/L-galactose pathway to ascorbate and the enzyme containing a point mutation in the vitamin C deficient vtc1-1 mutant (Conklin et al., 1999), are shown at the right.

The invention provides methods of increasing the growth rate, the aboveground and belowground biomass, and the stress tolerance of plants. This is accomplished by manipulating the expression of enzymes of the ascorbic acid-cell wall metabolic network in order to direct the flow of intermediates in the network. The invention provides an important addition to renewable energy and food production strategies, the methods being directly applicable to crop species and trees of economical and environmental importance. In addition, the concomitant enhancement of belowground biomass significantly contributes to carbon sequestration to lower tropospheric greenhouse gases.

The invention involves genetically engineering a plant to contain and over-express at least one gene of the ascorbic acid synthesis-cell wall synthesis network, and further provides transgenic plants that are genetically engineered in this manner. Without being bound by theory, the strong interconnection of the AsA biosynthetic pathway and the non-cellulosic cell wall biogenesis pathway (see FIG. 1) together with the experimental results obtained (see Examples section) suggest that transgenic plants that are genetically engineered to over-express at least one gene of the ascorbic acid synthesis-cell wall synthesis network have a more robust growth of the aboveground and belowground biomass of the plant, as well as increased tolerance to stress, as intermediates of the ascorbic acid route are diverted to pathways that promote biomass growth and tolerance to stress.

By "increase in growth rate" we mean that the plant increases its wet and/or dry biomass at a rate that is more rapid than that of a comparable, control plant that has not been genetically engineered in the manner herein described. In other words, the genetically engineered plant takes less time than the control plant to accumulate a particular biomass. Those of skill in the art are familiar with determining the significance of experimental results by comparison to suitable controls. In addition, the genetically engineered plant may ultimately exhibit a biomass that is greater than could be achieved by a corresponding control plant, no matter how long the control plant was allowed to grow. Further, the time to maturation of the genetically engineered plant may also be accelerated, i.e. the hallmarks of maturation (such as the production of fruit, seeds, etc.) may appear sooner in the genetically engineered plant than in a control plant, i.e. the rate of maturation may also be accelerated. In general, the level of increase in growth rate of the plant will be in the range of from at least about 10 to at least about 100%, and preferably from at least about 25 to at least about 75%, and most preferably, the increase will be at least about 50% above the level of expression in a control plant.

By "increased tolerance of stress" or "increased stress tolerance" we mean that the plant exhibits the ability to grow in a manner that is more successful than comparable control plants that are not genetically engineered as described herein, even under circumstances or conditions of stress for the plant. In other words, the genetically engineered plant is able to develop more or less normally with respect to growth rate, biomass, color, maturation, fruit production, etc, even under conditions of stress. Factors contributing to conditions of stress for plants include but are not limited to: increases in soil or water salinity, lack of nutrients, air pollution, extreme cold or hot temperatures, photo-oxidation, and osmotic stress (e.g. drought, excessive wetness), etc. Under adverse, stressful conditions, plants that are genetically engineered according to the methods of the present invention maintain a growth rate and/or accumulate biomass and/or achieve a final biomass that is at least about 10 to about 100% greater than control plants, and preferably at least about 25 to at least about 75% greater, and most preferably, at least about 50% greater than control plants grown under the same conditions.

By "transgenic plant that is genetically engineered to overexpress at least one gene of the AsA synthesis-cell wall synthesis network" we mean that the transgenic plant has been genetically engineered or modified to contain and express at least one gene of the ascorbic acid synthesis-cell wall synthesis network at a level that is higher than the level of expression of the corresponding gene in matched, control plants that have not been genetically engineered in this manner. This may be accomplished in any of several ways that are known to those of skill in the art, e.g. by introducing one or more genes of the network that are not typically found in the plant (e.g. heterologous genes); by introducing multiple copies of genes of the network that are already in the plant (e.g. homologous genes); by adding genes or DNA sequences that are not in the network but which cause increased expression of genes in the pathway (e.g. promoter sequences, transcription factors, regulatory proteins, etc.). In general, the level of increase in expression of the gene will be in the range of from at least about 10 to at least about 100%, and preferably from at least about 25 to at least about 75%, and most preferably, the increase will be at least about 50% above the level of expression in a suitable control plant.

By "transgenic plants that have been genetically engineered or modified" we mean that the plants have been genetically engineered to contain DNA that is not found in the plant prior to the genetic modification; or that is not found in the plant in the same form or in the same amount as prior to the genetic modification; or that is not expressed at as high a level prior to the genetic modification. For example, a gene encoding an enzyme from another source (e.g. a heterologous gene from another organism, or from another plant species or variety) may be purified from the source and manipulated by well-known molecular biology techniques so as to be suitable for insertion into and expression in plant cells. For example, a gene from the ascorbic acid synthesis-cell wall synthesis network may be isolated and purified from *Arabidopsis thaliana*, cloned and manipulated using molecular biology techniques, inserted into a suitable vector, and then used to transform plant cells from another plant (e.g. tobacco, lettuce, etc.). Alternatively, the genetic modification may involve cloning of a gene from a plant species, genetic manipulation of the gene, and reinsertion and expression of the gene into the same species of plant. Thus, the transgenic plant may, prior to genetic manipulation, contain a gene encoding the same or a similar enzyme with which is it genetically transformed. Alternatively, the gene may be present in the transgenic plant in the same form and at a similar level, but with a genetic alteration (e.g. with a super promoter cloned into the gene) that increases the level of expression of the gene in the plant. In addition, multiple copies of the gene may be introduced. Further, a combination of the above approaches may be used. In any case, the genetic modification contemplated by this invention confers the advantage of the gene product being over expressed in a manner that increases the growth rate and/or biomass and/or stress tolerance of the transgenic plant.

The gene or genes which are used to carry out genetic modification according to the present invention are those which encode enzymes of the AsA synthesis-cell wall synthesis network. This network is depicted in FIG. 1. Examples of enzymes that may be used in the practice of the present invention include but are not limited to glucuronic acid reductase (GlcUA reductase, At2g37770), gulono-1,4-lactone oxidase (GLOase, D12754), and myo-inositol oxygenase (MIOX, AY232552). In preferred embodiments, the enzymes are GlcUA reductase, GLOase, and MIOX.

Those of skill in the art will recognize that there are many sources of the genes that are used to transform plants according to the methods of the present invention. Examples include but are not limited to plants, mammals, yeast, fungi and bacteria. Preferably, the source of the genes will be plants.

The present invention also provides plant GlcUA reductase enzymes and the genes that encode such enzymes. Exemplary nucleotide and amino acid sequences of such a plant GlcUA reductase enzyme from *Arabidopsis* are provided in FIGS. 7A and B, respectively. The invention provides such nucleotide in an isolated and substantially purified form, i.e. so far as is possible under standard laboratory procedures, the gene is cloned and isolated from a suitable source, and free of extraneous material, such as other genes, proteins, etc. In general, the gene will be at least about 50% purified, and preferably at least about 75% purified, and most preferably at least about 95% or more purified (e.g. based on dry weight) from other organic components. It should be understood that such isolated and purified genes may include such entities as buffering molecules, salts, reaction components, etc., that are typically present in suspension media used in laboratory purification schemes, for storage of "purified" genes, and for various genetic manipulations. Further, the gene itself may be included in a vector, particularly a vector that is suitable for genetic manipulations, or for translation of the gene product. In addition, both the DNA and RNA (e.g. MRNA) forms of the gene are included in the invention. The invention also provides the gene product translated from the cloned gene, both in a form that is purified, for example, in a laboratory setting (e.g. substantially free from other organic components as described for the gene above) or translated within a transgenic plant into which it has been introduced by genetic engineering techniques.

The present invention also provides transgenic plants modified by the methods of the present invention. The plants to be genetically modified may be any of a wide variety of types, including but not limited to *Arabidopsis*, tobacco, potato and lettuce. Preferably, the plants that are so modified are *Arabidopsis*, tobacco, potato and lettuce. Preferably, the gene(s) that is/are inserted into the transgenic plants encode enzyme which include but are not limited to glucuronic acid reductase (GlcUA reductase, At2g37770), gulono-1,4-lactone oxidase (GLOase, D12754), and myo-inositol oxygenase (MIOX, AY232552). In preferred embodiments, the enzymes are GlcUA reductase, GLOase, and MIOX. In particular, a transgenic plant transformed with plant GlcUA reductase, for example, with the nucleotide sequence represented in FIG. 7A, SEQ ID NO: 7) and expressing an active GlcUA reductase enzyme (for example, an enzyme with an amino acid sequence as represented in FIG. 7B, SEQ ID NO: 8) is contemplated.

By transgenic "plant" we mean the "plant" as is commonly understood, including, for example; a stalk, vine or trunk; root system; and leaves. However, also encompassed in the meaning of "plant" are various other parts of the plant, e.g. any reproductive portions of the plant (such as fruit, cones, pods, flowers, etc.), and including such components as seeds, pollen, ovules, and the like. Further, offspring of the transgenic plants are also encompassed in this meaning, regardless of the method of propagation (e.g. by sprouting seeds, by rooting leaves, bulbs, tubers, etc.).

Those of skill in the art will recognize that the precise sequence of a gene that is used in the practice of the present invention may vary from plant to plant due to differences between species or varietal variation in sequence, or even due to changes made via genetic engineering. For example, alterations in the DNA sequence may be made for any of several reasons (for example, to produce a convenient restriction enzyme site or to alter the stability of the MRNA) with or without affecting the amino acid sequence of the polypeptide translation product. Changes may be made which alter the amino acid sequence of the polypeptide (either purposefully to change the polypeptide sequence, or inadvertently due to a desired change in the DNA sequence) which still result in the expression of a suitable, functional enzyme. All such variants of the genes in the network are intended to be encompassed by the present invention. In general, the genes will display significant homology to the genes first identified in *A. thaliana*, preferably from about 50 to 100% homology, and more preferably about 75 to 100% homology, and most preferably from about 80, 85, 90 or 95% to 100% homology, so long as a suitable level of enzymatic activity of the enzymic gene product is maintained. Also included are nucleotide sequences that hybridize to the *A. thaliana* gene under conditions of high stringency, and proteins or polypeptides that are produced therefrom.

Likewise, the polypeptide that is encoded by one of the genes of interest may vary in translated primary sequence. However, in general, they will display about 50 to 100% homology to the enzymes isolated from *A. thaliana*, and preferably about 75 to 100% homology, or even from about 80, 85, 90 or 95% to 100% homology, and will retain a level of activity that is sufficient to promote and sustain increased growth rate, biomass and stress tolerance of the transformed plant. Variations in amino acid sequence may be due to any of a number of factors, including substitutions (both conservative and non-conservative), deletions, insertions, etc. in the nucleic acid sequence that encodes the enzyme, alterations that are introduced by genetic engineering, and post-translational modifications. Amino acids may be deleted from the amino or carboxyl terminus of the polypeptide, or new sequences (e.g. targeting sequences) may be added to the polypeptide, or changes may be made to alter the stability of the protein. Alternatively, variations may also reflect inter-species or inter-varietal variations. The means of determining homology between nucleic acid sequences or between amino acid sequences are well known to those of skill in the art.

The methodology for creating transgenic plants is well developed and well known to those of skill in the art. For example, dicotyledon plants such as soybean, squash, tobacco (Lin et al. 1995), and tomatoes can be transformed by *Agrobacterium*-mediated transformation. (Miesfeld, 1999, and references therein). In this method, special laboratory strains of the soil bacterium *Agrobacterium* are used as a means to transfer DNA material directly from a recombinant bacterial plasmid into the host cell. DNA transferred by this method is stably integrated into the genome of the recipient plant cells, and plant regeneration in the presence of a selective marker (e.g. antibiotic resistance) produces transgenic plants.

Alternatively, for monocotyledon plants, such as rice (Lin and Assad-Garcia, 1996), corn, and wheat which may not be susceptible to *Agrobacterium*-mediated transformation, genes may be inserted by such techniques as microinjection, electroporation or chemical transformation of plant cell protoplasts (Paredes-López, 1999 and references therein), or particle bombardment using biolistic devices (Miesfeld, 1999; Paredes-López, 1999; and references therein). Monocotyledon crop plants have now been increasingly transformed with *Agrobacterium* (Hiei, 1997) as well.

In order to insert a gene of the network into a host plant, the gene may be identified, isolated and incorporated into a suitable construct such as a vector. Techniques for manipulating DNA sequences (e.g. restriction digests, ligation reactions, and the like) are well known and readily available to those of skill in the art. For example, Sambrook et al., 1989. Suitable vectors for use in the methods of the present invention are well known to those of skill in the art.

Further, such vector constructs may include various elements that are necessary or useful for the expression of the gene of interest. Examples of such elements include promoters, enhancer elements, terminators, targeting sequences, and the like. For example, a non-native (i.e. not associated with the gene in nature) constitutive or "strong" promoter sequence may be added in order to cause increased levels of expression of the gene. Similarly, an inducible promoter responsive, for example, to environmental conditions such as oxidative stress, may be inserted in order to make selective expression of the gene possible. Other types of genetic modifications that may be used to genetically modify the genes of interest of the present invention include but are not limited to the addition of developmentally regulated promoters to make possible selective expression at a particular time and/or location within the plant. All such potential genetic modifications are intended to be encompassed by the present invention, and any such useful elements may be incorporated into the constructs which house the gene of interest in the practice of the present invention. Further, those of skill in the art will recognize that a plant may be genetically modified to contain more than one gene of interest (i.e. several different genes of interest), and a single gene of interest may be present in more than one copy in the plant. Further, multiple copies of one gene of interest may be included in a single construct, or copies of more than one gene of interest may be included on a single construct. The gene(s) of interest may be retained in the host plant extrachromosomally, or may be integrated into the host plant genome.

Those of skill in the art will recognize that a wide variety of plants exist to which the technology of the present invention may be applicable. Examples include but are not limited to: crops grown for food production for humans or other animals (e.g. wheat, rice, canola, sunflowers, tomatoes, strawberries, apples, peaches, pears, etc.); crops grown for fuel (e.g. corn, soybeans, etc.); ornamental plants such as bedding plants and roses; trees that are used for fuel, building, etc. such as hybrid poplar, pine cedar; and fiber crops such as cotton hemp, flax, kanaf, etc. Further, plants that are genetically engineered according to the methods of the present invention may also be genetically engineered to exhibit other traits as well, e.g. pest or pesticide resistance, salt tolerance, or resistance to oxidative stress. In sum, any plant capable of being genetically engineered as described herein, in a manner that results in increased growth rate and/or biomass and/or stress tolerance, or any combination of theses traits.

Due to the increased underground biomass of the transformed plants of the present invention, such plants (e.g. trees) possess the ability to sequester large amounts of carbon from the atmosphere. Thus, the invention also provides a method of sequestering carbon by genetically engineering plants, especially trees, to contain and express a functional gene of the AsA biosynthesis-cell wall biosynthetic network.

EXAMPLES

Example 1

Increasing Biomass in Plants with Altered AsA Synthesis

L-Ascorbic acid is a major antioxidant molecule, an essential cofactor for several important metal-containing enzymes and is implicated in control of cell division and growth (Smirnoff and Wheeler, 2000; Davey et al., 2000; Arrigoni and de Tullio, 2002). Although AsA plays numerous critical roles in plant growth and development, a biosynthetic pathway for this versatile compound was not elucidated until 1998 (Wheeler et al.). Since that time, several research groups have discovered additional routes for synthesis and a complex network for producing ascorbic acid is now recognized. The major pathways include: D-mannose/L-galactose (Man/Gal) (Wheeler et al., 1998), D-galacturonate (Agius et al., 2003), and myo-inositol (MI) (Lorence et al., 2004). In addition, in a branch pathway of the Man/Gal route, UDP-mannose-3,5-epimerase appears to function under stress conditions (Wolucka and van Montagu, 2003).

The MI route to ascorbate is initiated by the MI oxygenase (MIOX) conversion of MI to D-glucuronic acid (GlcUA), and continued by reduction of GlcUA to L-gulonate to L-gulono-1,4-lactone by gluconolactonase and to ascorbic acid by gulono, 1,4-lactone oxidase (GLOase). However, in addition to its role in ascorbic acid biogenesis in plants, the oxidation of MI to GlcUA forms part of what is called the MI oxidation pathway (MIOP) for cell wall formation in seedlings, MI appearing to be the major source of the branch point GlcUA. The presence of MIOP has been demonstrated in a wide variety of plant species and tissues (Loewus and Murthy, 2000). MIOP involves cyclization of D-glucose-6-phosphate to inositol-3-phosphate, loss of phosphate to form MI, oxidation of MI to GlcUA, phosphorylation at carbon 1, and conversion to UDP-D-GlcUA. Alternatively, D-glucose-6-P is converted to UDP-D-glucose, which undergoes oxidation to UDP-D-GlcUA, a process named the sugar nucleotide oxidation pathway (SNOP). UDP-GlcUA is the central intermediate in the inter-conversion pathway to other nucleotide sugars, including UDP-derivatives of arabinose, xylose, apiose and galacturonic acid which account for half the biomass of a typical *Arabidopsis* leaf cell wall (Seitz et al., 2000). Both UDP-D-GlcUA and its product of decarboxylation, UDP-D-xylose, strongly inhibit $NAD^+$ dependent UDP-D-glucose dehydrogenase (UGD), the enzyme that oxidizes UDP-glucose to UDP-D-GlcUA.

GlcUA thus constitutes a branch point between cell wall and AsA biosynthesis. Additional branching points between AsA and cell wall formation are GDP-Man and GDP-Gal. FIG. 1 depicts the ascorbate (*) and cell wall polysaccharide biogenesis (☆) network. The mannose/L-galactose pathway to ascorbate and the enzyme containing a point mutation in the vitamin C deficient vtc1-1 mutant (Conklin et al., 1999), are shown at the right.

Figure 2:
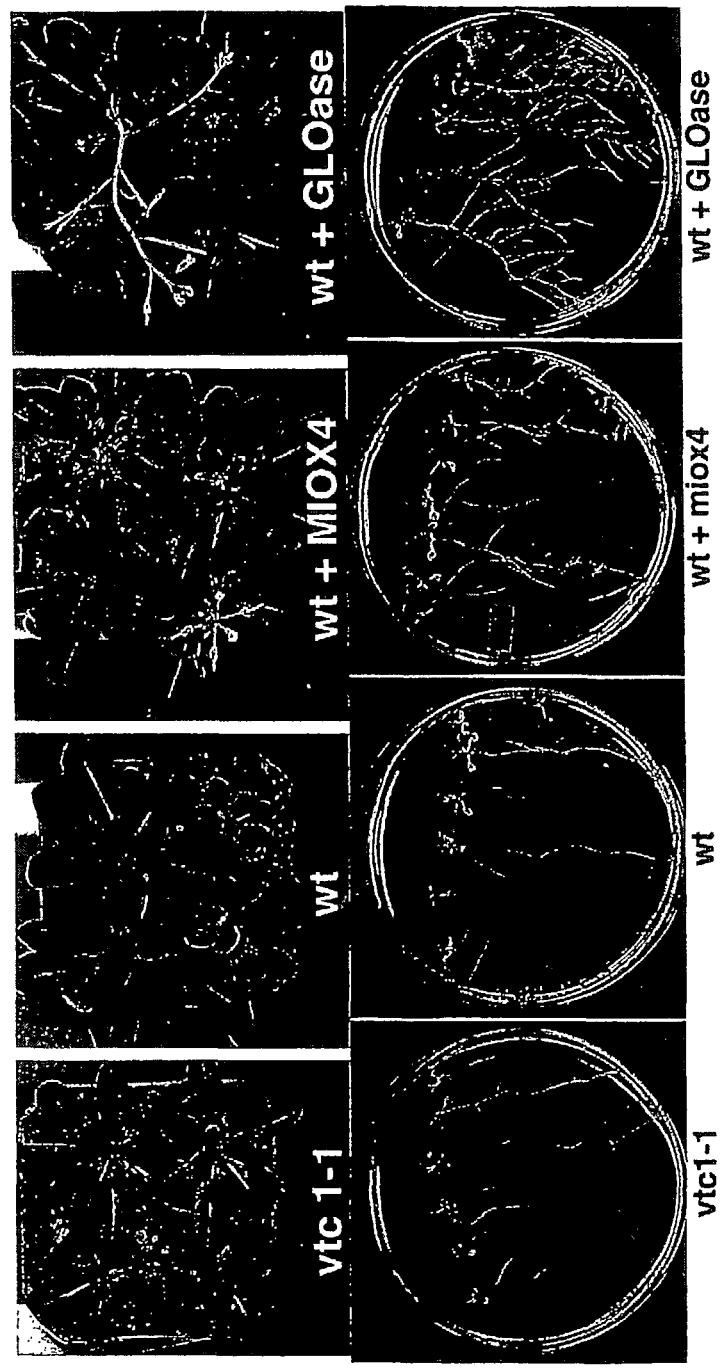
FIG. 2. Phenotype of foliar and root organs of MIOX4 and GLOase over-expressing lines compared to wild type (wt) and vitamin C-deficient vtc1-1 Arabidopsis thaliana plants. Plants were grown in a controlled environment chamber at 251° C., 150 µmol m$^{-2}$ s$^{-1}$, 60% humidity and 16/8 photoperiod.

A suite of *Arabidopsis* homozygous mutants involved in AsA synthesis has been developed. These mutants over-express key enzymes in the MI route to ascorbate. An unexpected observation in experiments with *Arabidopsis* homozygous lines where the enzymes that "push" (MIOX4) or "pull" (GLOase) the MI pathway to AsA are over-expressed, has been a more robust growth of the aboveground and belowground biomass when compared to wt or vitamin C deficient vtc1-1 *Arabidopsis* plants growing under similar conditions. Results from such an experiment are presented in FIG. 2, which shows the phenotype of foliar and root organs of MIOX4 and GLOase over-expressing plants lines, compared to wt and vitamin C-deficient vtc1-1 *Arabidopsis* plants. As can be seen, plants with elevated ascorbic acid show a more robust growth of both above and below ground tissues.

Figure 3:
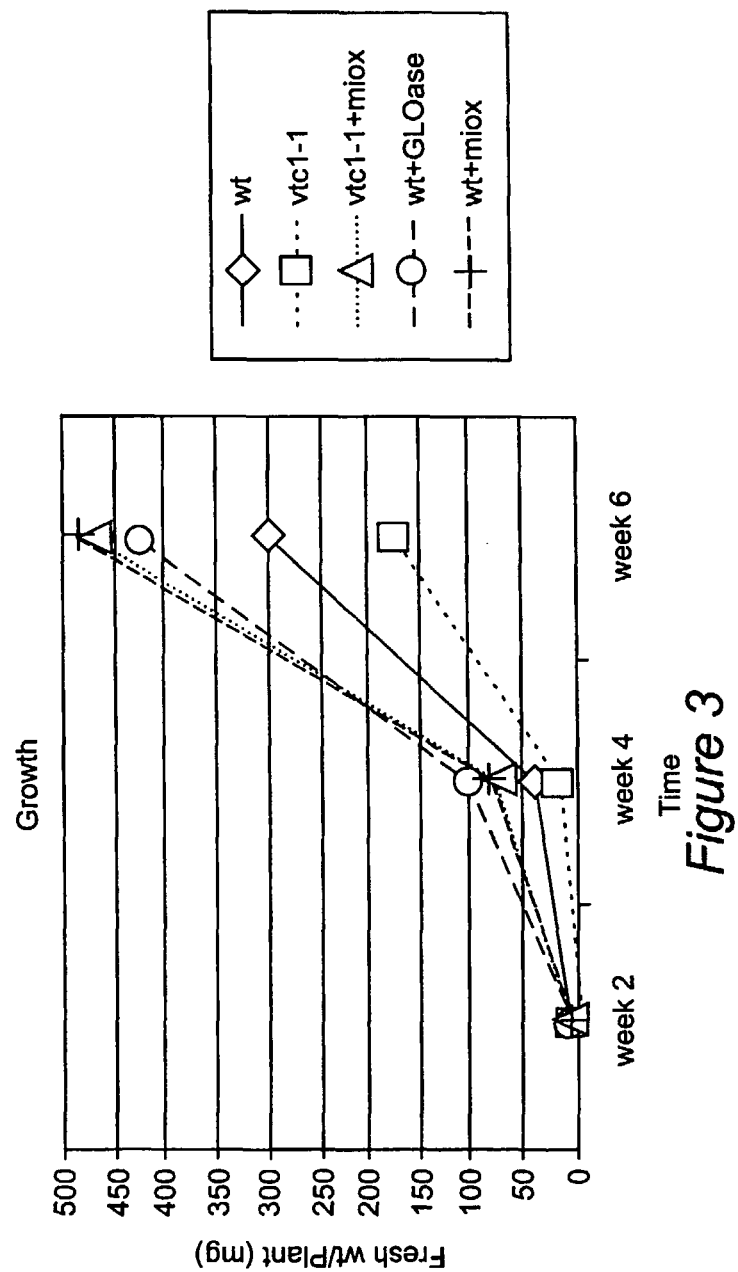
FIG. 3. Mean biomass (wet weight) of MIOX4 and GLOase over-expressing lines compared to wild type (wt) and vtc1-1 Arabidopsis plants. Plants were grown as described in FIG. 2, n=4.

Based on these observations, further experiments were carried out to obtain quantitative data on the fresh weight and dry weight of these transgenic plants. FIG. 3 shows fresh weight data from a 6-week experiment with wt and ascorbic acid deficient mutant vtc1-1, as well as these same genotypes transformed with the rat GLOase and MIOX genes expressed from the 35S promoter. As can be seen, the fresh weight of the vtc1-1 mutant is reduced relative to wt, which is well documented by us and others. However, both vtc1-1 and wt plants show a 50% increase in growth as a result of expressing either GLOase or MIOX.

Figure 4:
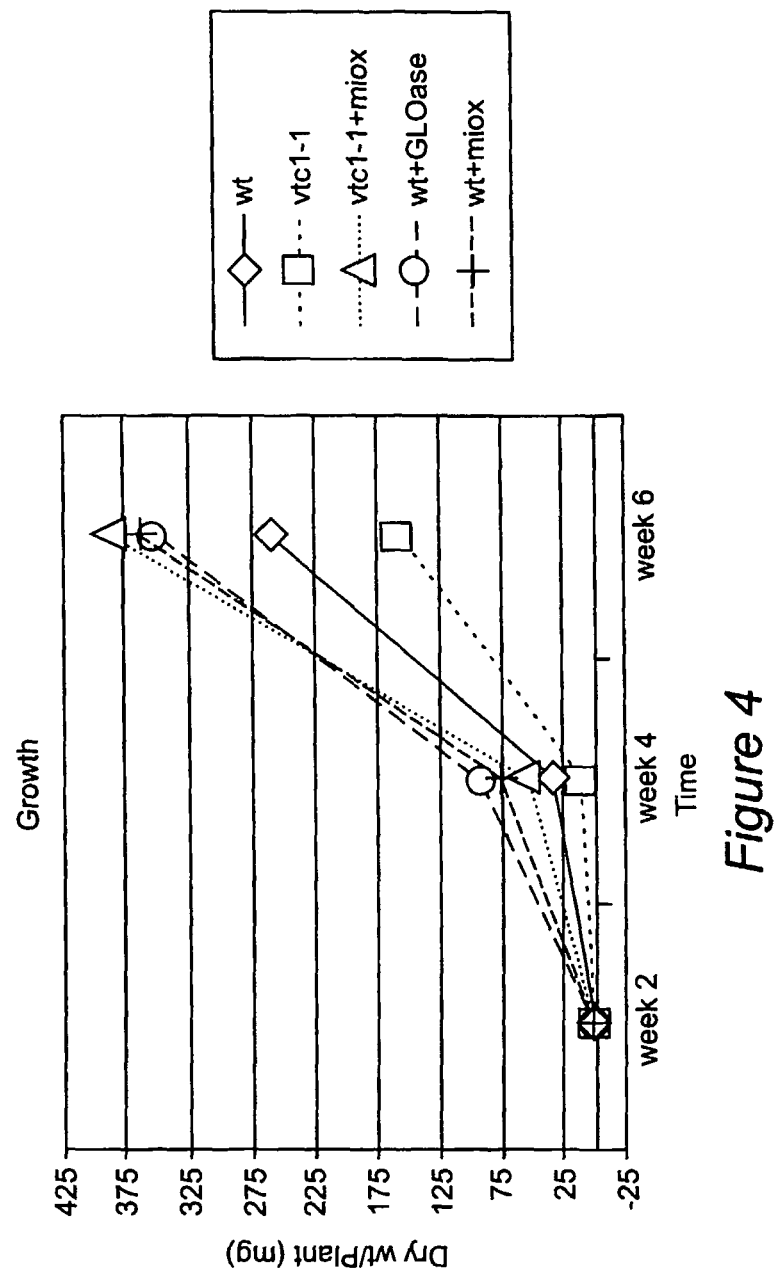
FIG. 4. Mean biomass (dry weight) of MIOX4 and GLOase over-expressing lines compared to wt and vtc1-1 Arabidopsis plants. Plants were grown as described in FIG. 2, n=4.

Similarly, FIG. 4 shows dry weight data from plants of the same genotypes. As can be seen, the dry weight of the vtc1-1 mutant is reduced relative to wt. However, both vtc1-1 and wt plants display a 50% increase in dry weight as a result of expressing either GLOase or MIOX. Similar results have been obtained in independent experiments carried out under greenhouse conditions with MIOX over-expressing lettuce (*Lactuca sativa* var. Black Seeded Simpson) lines, and with GlcUA reductase vtc1-1 over-expressing lines (data not shown).

Figure 5:
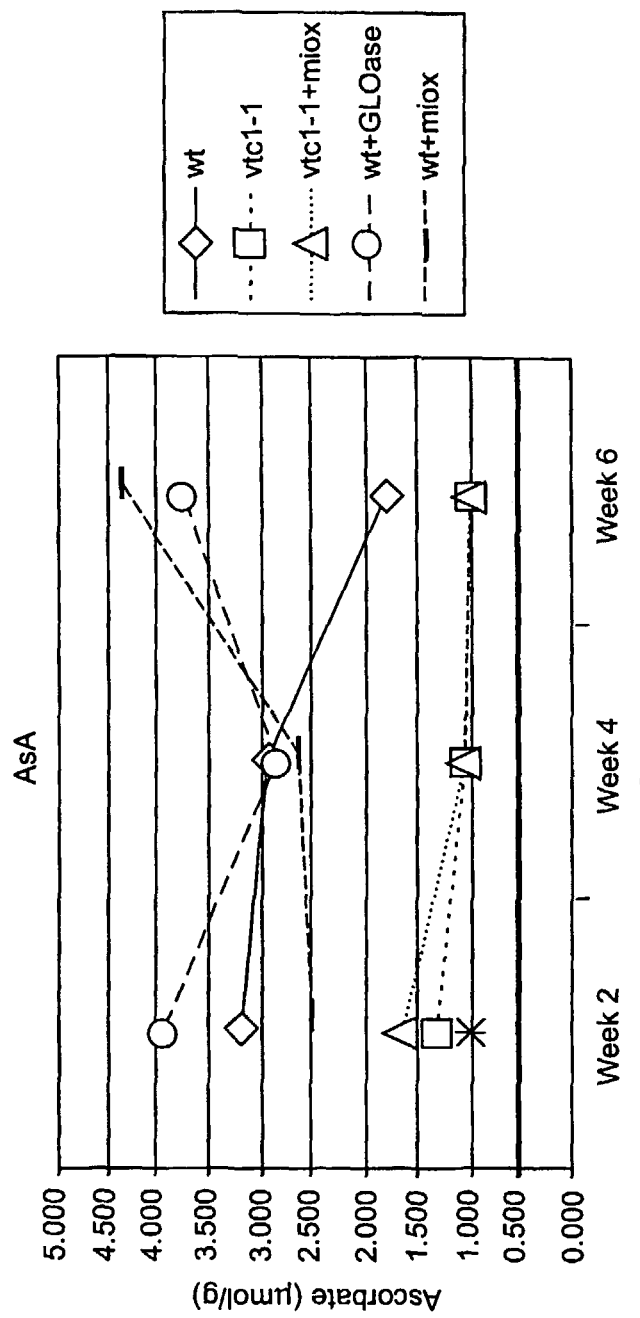
FIG. 5. Vitamin C data of MIOX4 and GLOase over-expressing lines compared to wt and vtc1-1 Arabidopsis plants. Plants were grown as described in FIG. 2, n=4.

Data regarding AsA levels that was obtained with both wt and ascorbic acid deficient mutant vtc1-1 suggest that the increases in wet and dry weight are not necessarily (may or may not be) due to higher AsA levels in these plants. FIG. 5 shows AsA data from a 6-week experiment with wt and AsA deficient mutant vtc1-1, both with and without transformation with the rat GLOase and MIOX genes expressed from the 35S promoter. As can be see, both the wt and vtc1-1 mutant have higher levels of AsA when expressing GLOase. However, unexpectedly, expression of MIOX, while increasing levels of AsA in wt plants, does not cause a recovery of AsA in vtc1-1. Further, it appears that the AsA levels in transgenic plants transformed with both MIOX and GLOase continue to rise over the time course of the experiment, whereas AsA levels declined in wt plants.

A comparison of the data of FIGS. 3, 4 and 5 reveals that the increase in wet and dry weight in plants transformed with either GLOase or MIOX (FIGS. 3 and 4) cannot be due only to higher AsA levels, since MIOX over-expressing plants do not exhibit increased ascorbic acid levels in wt or vtc1-1 backgrounds (FIG. 5).

The data presented in this example demonstrates that increasing expression of genes encoding enzymes in the AsA-cell wall metabolic network results in more rapid and robust growth in plants, and that these effects do not necessarily result in an increased AsA content, depending on the genetic background of the plants, and thus may not be due to any accompanying rise in AsA. This is a novel discovery with great implications for plant development, energy production and for sustainable agriculture.

Example 2

Increasing Stress Tolerance in Plants with Altered AsA Synthesis-Cell Wall Synthesis Network Gene Expression Plants must coordinate metabolism and growth between various cells, tissues and organs; and, since they lack motility plants require built-in defenses against both biotic and abiotic stresses. In addition, plant cell metabolism is highly sequestered into membrane-bound organelles and primary metabolism is characterized by redundancy with there often being multiple routes leading to the same end.

As an antioxidant, elevated AsA may provide protection against a variety of stresses including air pollution, extreme cold or hot temperatures, photo-oxidation, and osmotic stress.

Figure 6:
FIG. 6. Effect of salt on wt and MIOX4 plants. Plants were grown in the greenhouse under ambient conditions and watered with either no salt (0 NaCl) or 150 mM NaCl. Higher salt tolerance was demonstrated by survival of the MIOX4 plants compared to wt.

Experiments carried out with *Arabidopsis* plants that overexpress the MIOX4 gene showed that the transgenic plants are tolerant to concentrations of exogenously applied salt (150 mM NaCl) that kills or severely damages wt plants. Typical results are shown in FIG. 6, where wt plants watered normally (i.e. with "0 NaCl") are shown in four containers on the left, and wt plants watered with 150 mM NaCl are shown in four middle containers, and MIOX4 transgenic plants watered with 150 mM NaCl are shown in the four containers on the right. As can be seen, the plants that over-expressed the MIOX4 gene exhibit a healthy phenotype similar to that of the wt control plants. In contrast, the wt plants watered with NaCl appear stunted and unhealthy.

This example demonstrates that expressing genes in the AsA synthesis-cell wall synthesis network are tolerant to biotic and abiotic stresses such as exposure to high salt.

MATERIAL AND METHODS (from Jain and Nessler, 2000; Lorence et al., 2004) Isolation of a myo-Inositol Oxygenase (MIOX) Insert from *Arabidopsis* Specific primers for the putative miox gene in chromosome 4 (miox4; GenBank AT4g2620) were designed with NcoI and BamHI sites added to the forward (MX4-5 CCCATGGCGATCTCTGTTGAG) (SEQ ID NO: 1) and reverse (MX4-3 CCGGATCCTCACCAC CTCAAG) (SEQ ID NO: 2) primers to facilitate subcloning. A 25 μL PCR reaction containing 3 μL of an *Arabidopsis* mixed tissue cDNA library (CD4-7) from the *Arabidopsis* Biological Resource Center (ABRC, Columbus, Ohio) as template was performed with proofreading polymerase (Pfu Turbo DNA polymerase, Stratagene, La Jolla, Calif.). After denaturation at 94° C. for 5 min, amplification was performed by 30 cycles of 1 min at 94° C., 1 min at 50° C. and 2 min at 72° C., followed by 5 min at 72° C. The 957 bp PCR fragment was cloned into the pGEM-T Easy vector (Promega, Madison, Wis.), amplified in *E. coli* DH5α and sequenced in both directions with T7 and SP6 primers using the ABI PRISM BigDye Terminator Cycle Sequencing Kit (PE Applied Biosystems, Foster City, Calif.).

```
Nucleotide sequence of cDNA encoding MIOX4 (GenBank AY232552)
                                                      (SEQ ID NO: 3)
  1 atgacgatct ctgttgagaa gccgattttt gaagaggttt ctgcattcga gaagagtggg 61 gacaatatcg gagagttgaa attggacgga ggattttcga tgccgaaaat ggacaccaat 121 gacgacgaag ctttttttggc tcctgagatg aatgcatttg gccgccaatt cagggactac 181 gatgttgaga gtgagaggca aaagggcgtc gaagagtttt acagattacg acacatcaac 241 caaactgtcg actttgtgaa aaagatgagg gctgaatatg gaaaattaga taaaatggtg 301 atgagcattt gggaatgttg tgagcttctc aatgaggttg tggatgagag tgatccagat 361 cttgacgagc cccagattca gcatttgctt caatctgccg aagccatccg caaagattac 421 cctaatgaag attggcttca tctgaccgct cttatccatg atcttgggaa agttattact 481 cttccacaat tcggaggact tcctcaatgg gctgttgttg gtgacacatt ccctgttgga 541 tgtgcatttg atgaatctaa cgtacatcac aagtactttg tggaaaaccc agattttcac 601 aacgaaacct acaacactaa aaatgggatt tactctgaag ggtgtggatt aaacaatgtc 661 atgatgtctt ggggccatga cgactacatg tacctggtgg ctaaagaaaa cggaagtacc 721 ttgccgtcgg ctggacagtt tatcataaga taccactcct tttacccttt gcacacggct 781 ggagaataca cccatcttat gaacgaggaa gacaaggaga atctgaagtg gctacacgtt 841 ttcaacaagt acgacttgta cagtaagagc aaagttcacg ttgatgtgga gaaggtcgag 901 ccttactaca tgtctcttat caagaaatat ttcccggaaa acttgaggtg gtga
```

Assembly of the GLOase Constructs.

An EcoRI fragment from the cDNA clone, GO15 (GenBank J03536), encoding GLOase was kindly provided by Dr. Morimitsu Nishikimi (Wakayama Medical College, Wakayama. Japan) (Koshizaka et al., 1988) The EcoRI insert from GO15 was used as a PCR template and a NcoI site was added at the translation start codon with the forward primer (5'-GGAACCATGGTCCACGGGTAC-3') (SEQ ID NO: 4). The reverse primer (5'TTAGTAGAAGACTTTCTCCAGG-TACGAATTCAAGAACATTCCA GTG-3') (SEQ ID NO: 5) was designed to add the missing 26 nucleotides at 3' end of the truncated EcoRI fragment.

Nucleotide sequence of partial cDNA encoding GLOase (GenBank J03536)

(SEQ ID NO: 6)

```
   1 ggatcctcct gatcactgga atcatggtcc atgggtacaa aggggtccag ttccaaaatt
  61 gggcaaagac ctatggttgc agtccagagg tgtactacca gcccacctcc gtggaggagg
 121 tcagagaggt gctggccctg gcccgggagc agaagaagaa agtgaaggtg gtgggtggtg
 181 gccactcgcc ttcagacatt gcctgcactg acggtttcat gatccacatg ggcaagatga
 241 accgggttct ccaggtggac aaggagaaga agcagataac agtggaagcc ggtatcctcc
 301 tggctgacct gcacccacag ctggatgagc atggcctggc catgtccaat ctgggagcag
 361 tgtctgatgt gacagttgct ggtgtcattg gatccggaac acataacaca gggatcaagc
 421 acggcatcct ggccactcag gtggtggccc tgaccctgat gacagctgat ggagaagttc
 481 tggaatgttc tgagtcaaga aatgcagatg tgttccaggc tgcacgggtg cacctgggtt
 541 gcctgggcat catcctcacc gtcaccctgc agtgtgtgcc tcagtttcag cttcaggaga
 601 catccttccc ttcgaccctc aaagaggtcc ttgacaacct agacagccac ctgaagaggt
 661 ctgagtactt ccgcttcctc tggtttcctc acactgagaa cgtcagcatc atctaccaag
 721 accacaccaa caaggccccc tcctctgcat ctaactggtt ttgggactat gccatcgggt
 781 tctacctact ggagttcttg ctctggacca gcacctacct gccatgcctc gtgggctgga
 841 tcaaccgctt cttcttctgg atgctgttca actgcaagaa ggagagcagc aacctcagtc
 901 acaagatctt cacctacgag tgtcgcttca agcagcatgt acaagactgg gccatcccta
 961 gggagaagac caaggaggcc ctactggagc taaaggccat gctggaggcc caccccaaag
1021 tggtagccca ctaccccgta gaggtgcgct tcacccgagg cgatgacatt ctgctgagcc
1081 cctgcttcca gagggacagc tgctacatga acatcattat gtacaggccc tatggaaagg
1141 acgtgcctcg gctagactac tggctggcct atgagaccat catgaagaag tttggaggaa
1201 gaccccactg ggcaaaggcc cacaattgca cccagaagga ctttgaggaa atgtacccca
1261 cctttcacaa gttctgtgac atccgtgaga agctggaccc cactggaatg ttcttgaatt
1321 cgtacctgga gaaagtcttc tactaaagca ggagtggaaa caaaccaccc tgacccctca
1381 cacttctgct gcccccgggg gtctggggag cagagaagtg cctcacaagc acaatgggaa
1441 ctgacctctc ctcctgacca caaagaaagg ctgggctctg gccgggtcc tctctgcctt
1501 cggcatcatt tcccttacat ccaggcgaag aagtggcctc tcactcaaat tcctgttagc
1561 atttccatgg gtcacacata aactgcaatc ctctcaggag aaggggatc cctgatacat
1621 catatctatc cagactaagg atgtggttct tcctagattc tatggctcca ccaggtatag
1681 agagattcct ggggcctgca gttctccatc cctcttcaga agggagggat cccttggcga
1741 gagtttggct cagaggtggc atgaagcatg ctctgctctc tcttaccctt gaaggtcctt
1801 cggatgccca gagatgtctg ctggtcctgg gcaagccatc attcaaacgg gtccaacctg
1861 gccttctgtc tgccatggcc tgaccctcgc agtgtctctt ccagaggtgt ttagagtgga
1921 actcgcttca acctcttaac cagttgctga tccctgtgtt tctctccctt ctccttggag
1981 actactcttg gagggggatc ccaccatgtc cttggctttc cctgggtatt gttctcctct
2041 tcctcttcac aaatatgatt tcagtttgat ttgtggcctt tctggagtgt tccttggaga
2101 accaagatgt tccagctacc
```

The 1.35 Kb PCR amplified fragment was cloned into NcoI and EcoRV sites of pGEM −5Zf(+) (Promega, Madison, Wis.) to create pGLO-1. The cloned PCR fragment was subcloned into NcoI and SacI sites of pRTL2 (Restrepo et al., 1990) to create pGLO-2 which places the GLOase insert under the control of CaMV 35S promoter with a dual enhancer, with the 5' tobacco etch virus leader and a 3' nopaline synthase terminator. The 35S::GLOase construct was subcloned into the Hind III site of the binary vector pBIN19 and electroporated into *Agrobacterium tumefaciens* LBA4404.

Plant Material and Growth Conditions

Seeds of *Arabidopsis thaliana* (ecotype Columbia) both wild type and transgenic homozygous lines were grown in Sunshine Mix #1 (Wetzel, Harrisonburg, Va.) in a greenhouse during the months of September to December of 2004. The greenhouse is equipped with supplemental light (mercury vapor) and a heat-pump to keep temperature and relative humidity conditions as follows: a 16:8 h protoperiod, photon flux density of 950 μmol $m^{-2}$ $s^{-1}$, temperature 26:18±2.5° C. (day:night), and relative humidity of 50:70±10% (day:night).

Construction of Transgenic MIOX Plants

The miox4 insert was cloned into the NcoI/BamH1 sites of pRTL2 placing it under the control of CaMV 35S promoter with duplicated enhancer between the 5' tobacco etch virus (TEV) leader and the 3' 35S polyadenylation signal (Rastrepo et al., 1990). A PstI fragment including the promoter::miox4:: terminator insert was sub-cloned into the binary vector pCAMBIA1300 and transformed into *Agrobacterium tumefaciens* strain GV3101. *A. thaliana* var. Columbia plants were transformed with pCAMBIA1300:miox4 construct via the floral dip method (Clough and Bent, 1998). Seedlings were selected on MS (Murashige and Skoog, 1962) plates containing 500 mg $L^{-1}$ carbenecillin and 25 mg $L^{-1}$ hygromycin. Both primary transformants and their progeny were used for RNA gel blot analysis and ascorbic acid assays.

Construction of Transgenic GLOase Plants

*A. thaliana* var. Columbia wt and vtc1-1 lines were transformed with 35S:GLOase construct described by Jain and Nessler (2000) via the floral dip method (Clough and Bent, 1998). The vtc1-1 mutant normally retains only 25-30% of the wt AsA leaf content. The normal VTC locus (VTC1) encodes GDP-Man pyrophosphorylase (GMPase, EC. 2.7.7.13, mannose-1-phosphate guanyl transferase (Conklin et al., 1999). Seedlings were selected on MS (Murashige and Skoog, 1962) plates containing 500 mg $L^{-1}$ carbenecillin and 100 mg $L^{-1}$ kanamycin. Both primary transformants and their progeny were used for RNA gel blot analysis and AsA assays.

Ascorbic Acid Measurements

Ascorbic acid content was measured by the ascorbate oxidase assay (Rao and Ormrod, 1995). Plant extracts were made from tissue frozen in liquid nitrogen, ground in 6% metaphosphoric acid, and centrifuged at 15,000 g for 15 min. Reduced AsA was determined by measuring the decrease in absorbance at 265 nm (extinction coefficient of 14.3 mM) after addition of 1 U of ascorbate oxidase (Sigma) to 1 mL of the reaction medium containing the plant extract and 100 mM potassium phosphate, pH 6.9. Oxidized AsA was measured in a 1 mL reaction mixture plus 1 μL of 2 mM DTT after incubating at room temperature for 15 mm.

Example 3

Identification and Cloning of Plant Glucuronic Acid Reductase (GlcUA Reductase)

There is evidence of the operation of at least two biosynthetic pathways for AsA in plants: the mannose/L-galactose pathway and a D-galacturonic acid pathway. In addition, a branch route that leads to the synthesis of intermediates also common to the "animal vitamin C pathway" has been recently described. Evidence for an additional route for AsA formation using myo-inositol (MI) as the initial substrate is known. A MI oxygenase (miox) gene was identified in chromosome 4 (miox4) of *Arabidopsis thaliana* ecotype Columbia, and its enzymatic activity was confirmed in bacterially expressed recombinant protein (Lorence et al., 2004). MIOX is an enzyme containing non-heme iron that catalyses a four-electron oxidation with the transfer of only one atom of oxygen into the product D-glucuronic acid (GlcUA). There are only two additional enzymatic steps necessary for the conversion of GlcUA to AsA. The first of those reactions is the reduction of GlcUA to L-gulonic acid. This conversion is catalyzed by a GlcUA reductase (EC 1.1.1.19), also called gulonate dehydrogenase or L-hexonate dehydrogenase. GlcUA reductase belongs to the family of aldo/keto reductases and has been extensively studied in mammalian models (Smirnoff, 2001 and references therein, however, there are no reports of its enzymatic activity in plants.

A database search revealed no plant enzymes annotated as GlcUA reductase (or any of its synonyms). An expanded analysis found that there are close to 40 members of the aldo/keto reductase family in the *Arabidopsis* genome. Screening of T-DNA knockout lines using HPLC and spectrophotometric-based assays of some of the members of the aldo/keto reductase family allowed identification of the SALK line 119576, which had a substantial reduction (~50%) of AsA leaf content compared to wild type plants. This line has a T-DNA inserted in ORF At2g37770. The ORF from *Arabidopsis* leaf cDNA has now been cloned. FIGS. 7A and B show the nucleotide sequence (SEQ ID NO: 7) and the amino acid sequence (SEQ ID NO: 8) of ORF At2g37770, respectively, which represents the first identification of a plant GlcUA reductase. An alignment of the amplified plant GlcUA reductase protein sequence versus the published At2g37770 sequence (GeneBank Accession No. AAC23647) revealed 5 amino acid changes at residues in positions 4, 5, 13, 261 and 262 (FIG. 8, where "Sbject 1" refers to the Gene Bank sequence, SEQ ID NO: 9; Query 1 refers to the *Arabidopsis* plant GlcUA reductase sequence, SEQ ID NO: 8); and the sequence positioned between Query 1 and Sbjct 1 represents the amino acids common to both sequences (SEQ ID NO: 10).

Figure 9:
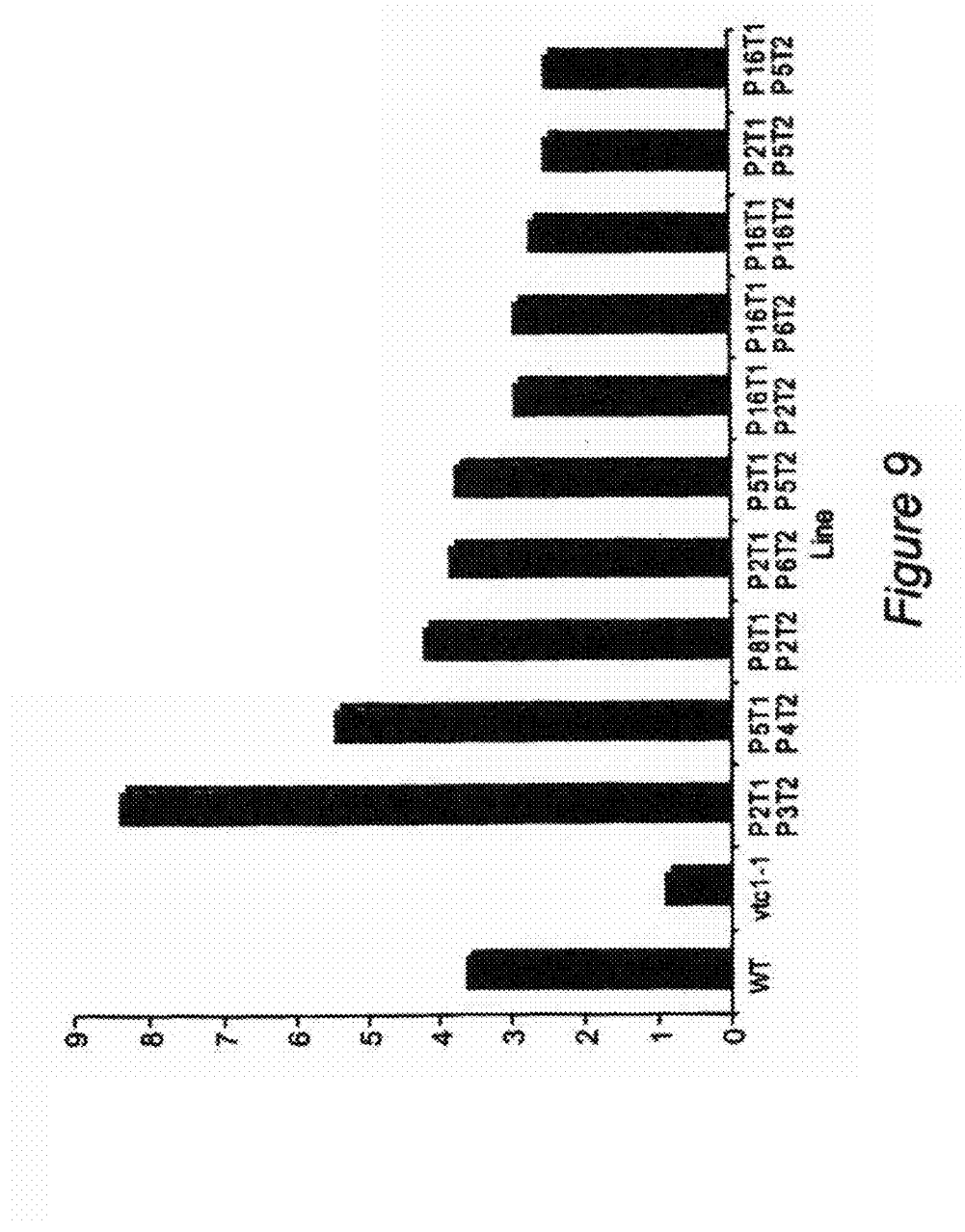

Over-expression of plant GlcUA reductase under the control of a strong constitutive promoter (e.g. CaMV 35S) in wt *Arabidopsis* plants led to an increase of 2-fold in the AsA content of the leaves. Additionally, constitutive expression of plant GlcUA reductase was able to restore both the phenotype and AsA level of the vitamin C deficient mutant vtc1-1, indicating the usefulness of this gene not only to manipulate AsA levels in plants, but also to enhance their growth (FIG. 9).

This example demonstrates that GlcUA reductase represents a powerful tool to manipulate vitamin C in plants and develop plants with increased growth rate, biomass accumulation and enhanced stress tolerance.

REFERENCES

Agius F, Gonzalez-Lamonthe R, Caballero J L, Muñoz-Blanco J, Botella M A, et al (2003) *Nat Biotechnol* 21:177-181

Arrigoni O, de Tullio M C (2002) *Biochim Biophys Acta* 1569: 1-9

Clough S J, Bent A F (1998) *Plant J* 16: 735-43

Conklin P L, Norris S R, Wheeler G L, Williams E H, Smimoff N, et al (1999) *Proc Natl Acad Sci* USA 96: 4198-4203

Davey M W, van Montagu M, Inze D, Sanmartin M, Kanellis A, et al (2000) *J Sci Food Agric* 80: 825-860

Hiei, Y et al. *Plant Mol. Biol.* 35, 205-218 (1997).

Jain A K, Nessler C L (2000) *Mol Breed* 6: 73-78
Lin, J J M, Assad-Garcia, N, Kuo K *Plant Sci.* 109, 171 (1995).
Loewus F A, Murthy P P N (2000) *Plant Sci* 150: 1-19
Lorence A, Chevone B I, Mendes P, Nessler C L (2004) *Plant Physiol* 134: 1200-1205
Miesfeld, R. L. *Applied Molecular Genetics*, Wiley-Liss, Publisher, pp. 205-235 1999.
Murashige T, Skoog F A (1962) *Physiol Plant* 15: 473-497
Paredes-López, ed. *Molecular Biotechnology for Plant Food Production*, Technomic Publishing, Inc. 1999.
Rao M, Ormrod D P (1995) *Photochem Photobiol* 61: 71-78
Rastrepo M A, Freed D D, Carringtom J C (1990) *Plant Cell* 2: 987-998
Sambrook J, Fritsch E F and Maniatis T, In Molecular Cloning: A Laboratory Manual, Second edition, Cold Spring Harbor Laboratory, Cold Spring Harbor, N.Y., 1989.
Seitz B, Klos C, Wurm M, Tenhaken R (2000) *Plant J* 21: 537-546
Smimoff N. (2001) *Vitam Horm* 61: 241-266.
Smimoff N, Wheeler G L (2000) *Crit Rev Biochem Mol Biol* 35: 291-314
Wheeler G L, Jones M A, Smimoff N (1998) *Nature* 393: 365-369
Wolucka B A, van Montagu M (2003) *J Biol Chem* 278: 47483-47490

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A method for increasing a growth rate, biomass or stress tolerance of a plant, comprising the steps of:
   genetically engineering said plant to contain and over-express an *Arabidopsis* glucuronic acid reductase enzyme with an amino acid sequence that comprises the amino acid sequence as set forth in SEQ ID NO: 8, and wherein overexpression of said glucuronic acid reductase enzyme in said genetically engineered plant results in increased vitamin C content in said genetically engineered plant as compared to a control plant of the same species lacking said *Arabidopsis* glucuronic acid reductase enzyme comprising the amino acid sequence as set forth in SEQ ID NO: 8,
   wherein said step of genetically engineering includes
   i) isolating and purifying a gene encoding said glucuronic acid reductase; and
   ii) transforming said plant with said gene encoding said glucuronic acid reductase,
   and wherein said step of genetically engineering said plant results in increasing one or more of said growth rate, biomass or stress tolerance of said genetically engineered plant as compared to a control plant of the same species lacking the amino acid sequence of SEQ ID NO: 8.

2. The method of claim 1, wherein said increase in biomass is dry biomass or wet biomass.

3. The method of claim 1, wherein said stress is salt stress.

4. A transgenic plant, wherein said transgenic plant is genetically engineered to contain and over-express an *Arabidopsis* glucuronic acid reductase enzyme having an amino acid sequence that comprises the amino acid sequence as set forth in SEQ ID NO: 8, wherein said genetically engineered transgenic plant has increased vitamin C content as compared to a control plant of the same species lacking the amino acid sequence of SEQ ID NO: 8, wherein said genetically engineered transgenic plant is transformed with a gene encoding said glucuronic acid reductase enzyme, and wherein said genetically engineered transgenic plant shows increased growth rate, biomass or stress tolerance as compared to a control plant of the same species lacking the amino acid sequence of SEQ ID NO: 8.

5. The genetically engineered transgenic plant of claim 4 wherein said genetically engineered transgenic plant exhibits increased biomass.

6. The genetically engineered transgenic plant of claim 5, wherein said increase in biomass is dry biomass or wet biomass.

7. The genetically engineered transgenic plant of claim 4, wherein said genetically engineered plant exhibits increased stress tolerance.

8. The genetically engineered transgenic plant of claim 7, wherein said stress is salt stress.

9. An isolated and purified nucleotide sequence encoding an *Arabidopsis* glucuronic acid reductase enzyme, wherein said isolated and purified nucleotide sequence comprises the nucleotide sequence as set forth in SEQ ID NO: 7, and wherein said isolated and purified nucleotide sequence is operably linked to a heterologous promoter.

10. The isolated and purified nucleotide sequence of claim 9, wherein said isolated and purified nucleotide sequence consists of the nucleotide sequence of SEQ ID NO: 7.

11. The genetically engineered transgenic plant of claim 4, wherein said gene encoding said glucuronic acid reductase has a nucleotide sequence that comprises the nucleotide sequence as set forth in SEQ ID NO:7.

12. The genetically engineered transgenic plant of claim 4, wherein said glucuronic acid reductase enzyme consists of the amino acid sequence as set forth in SEQ ID NO: 8.

13. The method of claim 1, wherein said glucuronic acid reductase enzyme consists of the amino acid sequence as set forth in SEQ ID NO: 8.

14. The method of claim 1, wherein said gene has a nucleotide sequence that comprises the nucleotide sequence as set forth in SEQ ID NO: 7.

15. The method of claim 1, wherein said gene consists of the nucleotide sequence as set forth in SEQ ID NO: 7 which is operably linked to a heterologous promoter.

16. The method of claim 1, wherein said step of transforming includes a step of inserting said isolated and purified gene into a vector and using said vector to transform said plant to obtain said genetically engineered plant.

17. The isolated and purified nucleotide sequence of claim 9, wherein said isolated and purified nucleotide sequence is further contained within a vector.

* * * * *

UNITED STATES PATENT AND TRADEMARK OFFICE
CERTIFICATE OF CORRECTION

| | | |
|---|---|---|
| PATENT NO. | : 9,000,267 B2 | |
| APPLICATION NO. | : 11/908551 | |
| DATED | : April 7, 2015 | |
| INVENTOR(S) | : Nessler et al. | |

It is certified that error appears in the above-identified patent and that said Letters Patent is hereby corrected as shown below:

In the Specification

Please insert the following paragraph in column 1, beginning at line 13:

--STATEMENT REGARDING FEDERALLY SPONSORED RESEARCH OR DEVELOPMENT
This invention was made with government support under Grant No. 2002-35321-11600 awarded by the U.S. Department of Agriculture and Grant No. IBN0118612 awarded by the National Science Foundation. The government has certain rights in the invention.--

Signed and Sealed this
First Day of March, 2016

Michelle K. Lee
*Director of the United States Patent and Trademark Office*

```
                        SEQUENCE LISTING

<160> NUMBER OF SEQ ID NOS: 10

<210> SEQ ID NO 1
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 1
cccatggcga tctctgttga g                                                    21

<210> SEQ ID NO 2
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 2
ccggatcctc accacctcaa g                                                    21

<210> SEQ ID NO 3
<211> LENGTH: 954
<212> TYPE: DNA
<213> ORGANISM: Arabidopsis thaliana

<400> SEQUENCE: 3
atgacgatct ctgttgagaa gccgattttt gaagaggttt ctgcattcga gaagagtggg          60
gacaatatcg gagagttgaa attggacgga ggattttcga tgccgaaaat ggacaccaat         120
gacgacgaag cttttttggc tcctgagatg aatgcatttg gccgccaatt cagggactac         180
gatgttgaga gtgagaggca aaagggcgtc gaagagtttt acagattacg acacatcaac         240
caaactgtcg actttgtgaa aaagatgagg gctgaatatg gaaaattaga taaaatggtg         300
atgagcattt gggaatgttg tgagcttctc aatgaggttg tggatgagag tgatccagat         360
cttgacgagc cccagattca gcatttgctt caatctgccg aagccatccg caaagattac         420
cctaatgaag attggcttca tctgaccgct cttatccatg atcttgggaa agttattact         480
cttccacaat tcggaggact tcctcaatgg gctgttgttg gtgacacatt ccctgttgga         540
tgtgcatttg atgaatctaa cgtacatcac aagtactttg tggaaaaccc agattttcac         600
aacgaaacct acaacactaa aaatgggatt tactctgaag ggtgtggatt aaacaatgtc         660
```

| | |
|---|---|
| atgatgtctt ggggccatga cgactacatg tacctggtgg ctaaagaaaa cggaagtacc | 720 |
| ttgccgtcgg ctggacagtt tatcataaga taccactcct tttacccttt gcacacggct | 780 |
| ggagaataca cccatcttat gaacgaggaa gacaaggaga atctgaagtg ctacacgtt | 840 |
| ttcaacaagt acgacttgta cagtaagagc aaagttcacg ttgatgtgga gaaggtcgag | 900 |
| ccttactaca tgtctcttat caagaaatat ttcccggaaa acttgaggtg gtga | 954 |

<210> SEQ ID NO 4
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 4

| | |
|---|---|
| ggaaccatgg tccacgggta c | 21 |

<210> SEQ ID NO 5
<211> LENGTH: 46
<212> TYPE: DNA
<213> ORGANISM: Artificial
<220> FEATURE:
<223> OTHER INFORMATION: synthetic oligonucleotide primer

<400> SEQUENCE: 5

| | |
|---|---|
| ttagtagaag actttctcca ggtacgaatt caagaacatt ccagtg | 46 |

<210> SEQ ID NO 6
<211> LENGTH: 2120
<212> TYPE: DNA
<213> ORGANISM: Arabidopsis thaliana

<400> SEQUENCE: 6

| | |
|---|---|
| ggatcctcct gatcactgga atcatggtcc atgggtacaa aggggtccag ttccaaaatt | 60 |
| gggcaaagac ctatggttgc agtccagagg tgtactacca gcccacctcc gtggaggagg | 120 |
| tcagagaggt gctggccctg cccgggagc agaagaagaa agtgaaggtg gtgggtggtg | 180 |
| gccactcgcc ttcagacatt gcctgcactg acgtttcat gatccacatg ggcaagatga | 240 |
| accgggttct ccaggtggac aaggagaaga agcagataac agtggaagcc ggtatcctcc | 300 |
| tggctgacct gcacccacag ctggatgagc atggcctggc catgtccaat ctgggagcag | 360 |
| tgtctgatgt gacagttgct ggtgtcattg atccggaaac acataacaca gggatcaagc | 420 |
| acggcatcct ggccactcag gtggtggccc tgacctgat gacagctgat ggagaagttc | 480 |
| tggaatgttc tgagtcaaga aatgcagatg tgttccaggc tgcacgggtg cacctgggtt | 540 |
| gcctgggcat catcctcacc gtcaccctgc agtgtgtgcc tcagtttcag cttcaggaga | 600 |
| catccttccc ttcgaccctc aaagaggtcc ttgacaacct agacagccac ctgaagaggt | 660 |
| ctgagtactt ccgcttcctc tggttttcctc acactgagaa cgtcagcatc atctaccaag | 720 |
| accacaccaa caaggccccc tcctctgcat ctaactggtt ttgggactat gccatcgggt | 780 |
| tctacctact ggagttcttg ctctggacca gcacctacct gccatgcctc gtgggctgga | 840 |
| tcaaccgctt cttcttctgg atgctgttca actgcaagaa ggagagcagc aacctcagtc | 900 |
| acaagatctt cacctacgag tgtcgcttca agcagcatgt acaagactgg gccatcccta | 960 |
| gggagaagac caaggaggcc ctactggagc taaaggccat gctggaggcc cacccaaag | 1020 |
| tggtagccca ctaccccgta gaggtgcgct tcacccgagg cgatgacatt ctgctgagcc | 1080 |
| cctgcttcca gagggacagc tgctacatga acatcattat gtacaggccc tatggaaagg | 1140 |

| | |
|---|---|
| acgtgcctcg gctagactac tggctggcct atgagaccat catgaagaag tttggaggaa | 1200 |
| gaccccactg ggcaaaggcc cacaattgca cccagaagga ctttgaggaa atgtacccca | 1260 |
| cctttcacaa gttctgtgac atccgtgaga agctggaccc cactggaatg ttcttgaatt | 1320 |
| cgtacctgga gaaagtcttc tactaaagca ggagtggaaa caaaccaccc tgacccctca | 1380 |
| cacttctgct gcccccgggg gtctggggag cagagaagtg cctcacaagc acaatgggaa | 1440 |
| ctgacctctc ctcctgacca caaagaaagg ctgggtctg ggccgggtcc tctctgcctt | 1500 |
| cggcatcatt tcccttacat ccaggcgaag aagtggcctc tcactcaaat tcctgttagc | 1560 |
| atttccatgg gtcacacata aactgcaatc ctctcaggag aagggggatc cctgatacat | 1620 |
| catatctatc cagactaagg atgtggttct tcctagattc tatggctcca ccaggtatag | 1680 |
| agagattcct ggggcctgca gttctccatc cctcttcaga agggagggat cccttggcga | 1740 |
| gagtttggct cagaggtggc atgaagcatg ctctgctctc tcttacccct gaaggtcctt | 1800 |
| cggatgccca gagatgtctg ctggtcctgg gcaagccatc attcaaacgg gtccaacctg | 1860 |
| gccttctgtc tgccatggcc tgaccctcgc agtgtctctt ccagaggtgt ttagagtgga | 1920 |
| actcgcttca acctcttaac cagttgctga tccctgtgtt tctctccctt ctccttggag | 1980 |
| actactcttg gaggggatc ccaccatgtc cttggctttc cctgggtatt gttctcctct | 2040 |
| tcctcttcac aaatatgatt tcagtttgat ttgtggcctt tctggagtgt tccttggaga | 2100 |
| accaagatgt tccagctacc | 2120 |

<210> SEQ ID NO 7
<211> LENGTH: 813
<212> TYPE: DNA
<213> ORGANISM: Arabidopsis thaliana

<400> SEQUENCE: 7

| | |
|---|---|
| atggcaaatc cgagcacatt tttcaagctc aacaccagcg ctaagttccc ttcggtgggt | 60 |
| cttggaacat ggcaagcttc tcctggcctc gtcggtgatg cagtcgccgc ggccgttaag | 120 |
| attggctatc gtcacattga ttgtgctcag atctatggca acgaaaaaga gattggggca | 180 |
| gttctgaaaa aattgtttga agacagagta gtgaaacgcg aggatttgtt catcacctcc | 240 |
| aaactctggt gtactgatca tgaccctcaa gatgtcccgg aggcattgaa cagaactctc | 300 |
| aaggatctgc agcttgaata cgtcgatctt tatctgatac actggcctgc acggataaag | 360 |
| aaaggttctg ttggaataaa gccagagaac cttttgcctg tagatattcc tagtacatgg | 420 |
| aaagcgatgg aagcactata cgattcgggc aaggcacgag ccataggtgt aagcaatttc | 480 |
| tctaccaaga aactagctga tctcttggag ttagctcgtg ttcctcctgc tgttaatcag | 540 |
| gtcgaatgtc atccttcttg gcgacaaact aagctacaag aattctgcaa atccaaaggg | 600 |
| gttcacctaa gtgcatactc gccattaggt tctccaggga caacatggct gaagagcgat | 660 |
| gttttgaaga acccgatact gaatatggtt gcggaaaaac tcggaaagag tcctgcgcaa | 720 |
| gtcgcccttc gttggggact ccaaatgggt cacagtgtgc ttcccaagag tacaaatgag | 780 |
| gatccaatca cgaattctgg atccgatacg taa | 813 |

<210> SEQ ID NO 8
<211> LENGTH: 270
<212> TYPE: PRT
<213> ORGANISM: Arabidopsis thaliana

<400> SEQUENCE: 8

```
Met Ala Asn Pro Ser Thr Phe Phe Lys Leu Asn Thr Ser Ala Lys Phe
1               5                   10                  15

Pro Ser Val Gly Leu Gly Thr Trp Gln Ala Ser Pro Gly Leu Val Gly
            20                  25                  30

Asp Ala Val Ala Ala Val Lys Ile Gly Tyr Arg His Ile Asp Cys
            35                  40                  45

Ala Gln Ile Tyr Gly Asn Glu Lys Glu Ile Gly Ala Val Leu Lys Lys
        50                  55                  60

Leu Phe Glu Asp Arg Val Val Lys Arg Glu Asp Leu Phe Ile Thr Ser
65                  70                  75                  80

Lys Leu Trp Cys Thr Asp His Asp Pro Gln Asp Val Pro Glu Ala Leu
                85                  90                  95

Asn Arg Thr Leu Lys Asp Leu Gln Leu Glu Tyr Val Asp Leu Tyr Leu
            100                 105                 110

Ile His Trp Pro Ala Arg Ile Lys Lys Gly Ser Val Gly Ile Lys Pro
        115                 120                 125

Glu Asn Leu Leu Pro Val Asp Ile Pro Ser Thr Trp Lys Ala Met Glu
    130                 135                 140

Ala Leu Tyr Asp Ser Gly Lys Ala Arg Ala Ile Gly Val Ser Asn Phe
145                 150                 155                 160

Ser Thr Lys Lys Leu Ala Asp Leu Leu Glu Leu Ala Arg Val Pro Pro
                165                 170                 175

Ala Val Asn Gln Val Glu Cys His Pro Ser Trp Arg Gln Thr Lys Leu
            180                 185                 190

Gln Glu Phe Cys Lys Ser Lys Gly Val His Leu Ser Ala Tyr Ser Pro
        195                 200                 205

Leu Gly Ser Pro Gly Thr Thr Trp Leu Lys Ser Asp Val Leu Lys Asn
    210                 215                 220

Pro Ile Leu Asn Met Val Ala Glu Lys Leu Gly Lys Ser Pro Ala Gln
225                 230                 235                 240

Val Ala Leu Arg Trp Gly Leu Gln Met Gly His Ser Val Leu Pro Lys
                245                 250                 255

Ser Thr Asn Glu Asp Pro Ile Thr Asn Ser Gly Ser Asp Thr
                260                 265                 270

<210> SEQ ID NO 9
<211> LENGTH: 263
<212> TYPE: PRT
<213> ORGANISM: Arabidopsis thaliana

<400> SEQUENCE: 9

Met Ala Asn Ala Ile Thr Phe Phe Lys Leu Asn Thr Gly Ala Lys Phe
1               5                   10                  15

Pro Ser Val Gly Leu Gly Thr Trp Gln Ala Ser Pro Gly Leu Val Gly
            20                  25                  30

Asp Ala Val Ala Ala Val Lys Ile Gly Tyr Arg His Ile Asp Cys
            35                  40                  45

Ala Gln Ile Tyr Gly Asn Glu Lys Glu Ile Gly Ala Val Leu Lys Lys
        50                  55                  60

Leu Phe Glu Asp Arg Val Val Lys Arg Glu Asp Leu Phe Ile Thr Ser
65                  70                  75                  80

Lys Leu Trp Cys Thr Asp His Asp Pro Gln Asp Val Pro Glu Ala Leu
                85                  90                  95

Asn Arg Thr Leu Lys Asp Leu Gln Leu Glu Tyr Val Asp Leu Tyr Leu
            100                 105                 110
```

Ile His Trp Pro Ala Arg Ile Lys Lys Gly Ser Val Gly Ile Lys Pro
            115                 120                 125

Glu Asn Leu Leu Pro Val Asp Ile Pro Ser Thr Trp Lys Ala Met Glu
        130                 135                 140

Ala Leu Tyr Asp Ser Gly Lys Ala Arg Ala Ile Gly Val Ser Asn Phe
145                 150                 155                 160

Ser Thr Lys Lys Leu Ala Asp Leu Leu Glu Leu Ala Arg Val Pro Pro
                165                 170                 175

Ala Val Asn Gln Val Glu Cys His Pro Ser Trp Arg Gln Thr Lys Leu
            180                 185                 190

Gln Glu Phe Cys Lys Ser Lys Gly Val His Leu Ser Ala Tyr Ser Pro
        195                 200                 205

Leu Gly Ser Pro Gly Thr Thr Trp Leu Lys Ser Asp Val Leu Lys Asn
    210                 215                 220

Pro Ile Leu Asn Met Val Ala Glu Lys Leu Gly Lys Ser Pro Ala Gln
225                 230                 235                 240

Val Ala Leu Arg Trp Gly Leu Gln Met Gly His Ser Val Leu Pro Lys
                245                 250                 255

Ser Thr Asn Glu Gly Arg Ile
            260

<210> SEQ ID NO 10
<211> LENGTH: 258
<212> TYPE: PRT
<213> ORGANISM: Arabidopsis thaliana

<400> SEQUENCE: 10

Met Ala Asn Thr Phe Phe Lys Leu Asn Thr Ala Lys Phe Pro Ser Val
1               5                   10                  15

Gly Leu Gly Thr Trp Gln Ala Ser Pro Gly Leu Val Gly Asp Ala Val
            20                  25                  30

Ala Ala Ala Val Lys Ile Gly Tyr Arg His Ile Asp Cys Ala Gln Ile
        35                  40                  45

Tyr Gly Asn Glu Lys Glu Ile Gly Ala Val Leu Lys Lys Leu Phe Glu
50                  55                  60

Asp Arg Val Val Lys Arg Glu Asp Leu Phe Ile Thr Ser Lys Leu Trp
65                  70                  75                  80

Cys Thr Asp His Asp Pro Gln Asp Val Pro Glu Ala Leu Asn Arg Thr
                85                  90                  95

Leu Lys Asp Leu Gln Leu Glu Tyr Val Asp Leu Tyr Leu Ile His Trp
            100                 105                 110

Pro Ala Arg Ile Lys Lys Gly Ser Val Gly Ile Lys Pro Glu Asn Leu
        115                 120                 125

Leu Pro Val Asp Ile Pro Ser Thr Trp Lys Ala Met Glu Ala Leu Tyr
    130                 135                 140

Asp Ser Gly Lys Ala Arg Ala Ile Gly Val Ser Asn Phe Ser Thr Lys
145                 150                 155                 160

Lys Leu Ala Asp Leu Leu Glu Leu Ala Arg Val Pro Pro Ala Val Asn
                165                 170                 175

Gln Val Glu Cys His Pro Ser Trp Arg Gln Thr Lys Leu Gln Glu Phe
            180                 185                 190

Cys Lys Ser Lys Gly Val His Leu Ser Ala Tyr Ser Pro Leu Gly Ser
        195                 200                 205

Pro Gly Thr Thr Trp Leu Lys Ser Asp Val Leu Lys Asn Pro Ile Leu

-continued

```
              210                 215                 220
Asn Met Val Ala Glu Lys Leu Gly Lys Ser Pro Ala Gln Val Ala Leu
225                 230                 235                 240

Arg Trp Gly Leu Gln Met Gly His Ser Val Leu Pro Lys Ser Thr Asn
                245                 250                 255

Glu Ile
```